United States Patent [19]

Vite et al.

[11] 4,205,084
[45] May 27, 1980

[54] CONTROL OF INSECTS WITH 2-ETHYL-1,6-DIOXASPIRO[4.4]NONANE

[75] Inventors: Jean P. Vite, Freiburg i. Breisgau; Ernst J. W. Francke, Reinbek, both of Fed. Rep. of Germany; Günther Ohloff, Bernex, Switzerland

[73] Assignee: Firmenich S.A., Geneva, Switzerland

[21] Appl. No.: 943,488

[22] Filed: Sep. 18, 1978

[30] Foreign Application Priority Data

Sep. 23, 1977 [GB] United Kingdom ............... 39828/77

[51] Int. Cl.² .............................................. A01N 9/28
[52] U.S. Cl. ................................... 424/285; 260/347.8
[58] Field of Search ....................... 260/347.8; 424/285

[56] References Cited
PUBLICATIONS

Ponomarev et al., Chemical Abstracts, vol. 48 (1954) 12731d–g.

Til et al., Chemical Abstracts, vol. 51 (1957) 12877c–e.
Ponomarev et al., Chemical Abstracts, vol. 77 (1972) 87283f.

Primary Examiner—Richard Raymond
Attorney, Agent, or Firm—Pennie & Edmonds

[57] ABSTRACT

The present invention relates to a composition for the control of insects of the order of *Pityogenes chalcographus* which comprises together with a carrier substance a compound of formula

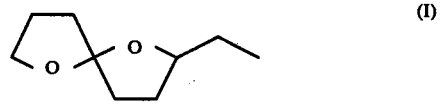

(I)

Method of attracting bark beetles of the said class. Process for the preparation of the spiro derivative of formula (I) starting from non-4-yn-1,7-diol.

3 Claims, No Drawings

CONTROL OF INSECTS WITH 2-ETHYL-1,6-DIOXASPIRO[4.4]NONANE

BACKGROUND OF THE INVENTION

Populations of the order of bark beetles, *Pityogenes chalcographus* [L.] infest Norway spruce, *Picea abies* [L.], recently creating a serious pest problem in European spruce stands. These beetles aggregate like other species of Pityogenes on standing trees or slash of freshly cut trees, in response to a pheromone released by the host-selecting male beetles. It is the object of the present invention to provide compositions containing a compound which causes the populations of *Pityogenes chalcographus* to aggregate in order to facilitate selective trapping.

THE INVENTION

The invention employs a compound of formula

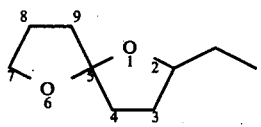

2-ethyl-1,6-dioxaspiro[4.4]nonane, and provides a composition for the control of insects of the order *Pityogenes chalocographus* which comprises a suitable carrier substance and the compound of formula (I).

The compound of formula (I) can be used in a method provided by the invention for attracting bark beetles species of the order *Pityogenes chalcographus* and which comprises permeating the atmosphere in an area infested with said beetles with an effective attractant amount of the compound of formula (I).

The compound (I), can, if desired, be employed as its diastereoisomers or enantiomers of formula

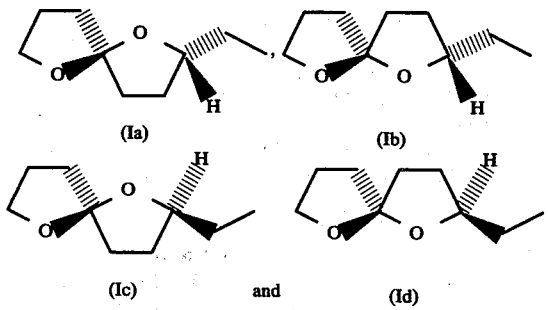

These optical isomers can be obtained by resolution of racemic compound (I).

The invention also provides a process for the preparation of the compound of formula (I), in its racemic form, which process comprises the step of cyclizing non-4-yn-1,7-diol in the presence of an acidic cyclizing agent.

The compound of formula (I), in its racemic form, can also be prepared by a process which comprises the step of alkylating 3-(fur-2-yl)-propionaldehyde by means of an ethyl-magnesium halide, followed by catalytic reductive cyclisation of the thus obtained 5-(fur-2-yl)-pentan-3-ol.

The present invention derives from our surprising finding that by evaporating in the atmosphere a communication effective amount of 2-ethyl-1,6-dioxaspiro[4.4]nonane, it was possible to attract in a chosen area a population of *Pityogenes chalcographus* with the obvious possibility of trapping them or anyhow of controlling their migration.

The compound of formula (I) can be applied at various concentration levels.

It can be used as such or as a composition in admixture with suitable carriers, such as for instance liquid or solid inert carriers, for example water, acetone, xylene, mineral or vegetable oils, talc or silica.

The evaporation can be effected by spraying or dusting, or simply by exposing freshly cut spruce bark preliminarly baited with 2-ethyl-2,6-dioxaspiro[4.4]nonane.

In the bioassays relatively large quantities of the active nonane (I) were used. These were of the order of about 15 mg/h.

The following table illustrates some of the results obtained by applying the method of the invention. Field response of *Pityogenes chalcographus* to tree trunk-simulating olfactometers baited with 2-ethyl-1,6-dioxaspiro[4.4]nonane was recorded.

TABLE

| Test material | Repetitions | Average number [and range] of beetles responding | Sex ratio Male:female |
|---|---|---|---|
| 2-ethyl-1,6-dioxaspiro [4.4]nonane on spruce bark | 4 | 23 [7–31] | 5.4:1 |
| 30 ♂ feeding in spruce log | | 29 [16–50] | 4.5:1 |
| spruce bark | | 1 [0–2] | |
| control (empty) | | 0 | |

The bioassays were carried out by making use of sleeve olfactometers [see Vité, J. P. et al., Can.Entomol., 101, 113 (1969)] in a spruce forest at Mooswald near Freiburg im Breisgau, West Germany on Apr. 22, 1977.

These assays show that 2-ethyl-1,6-dioxaspiro[4.4]nonane, in combination with fresh spruce bark, was almost as attractive as spruce log in which 30 male beetles had been feeding for 48 h.

According to the preparative process of the invention, racemic compound of formula (I) is prepared by cyclizing non-4-yn-1,7-diol by means of an acidic cyclizing agent.

The said cyclization can be effected by usual acidic cyclizing agents currently used for triple bond hydration [see e.g.: Org.Synth.Coll. vol. 4, 13 (1963)]. Typically, mercury oxide in an acidic medium such as concentrated or dilute sulfuric acid is satisfactory employed.

Non-4-yl-1,7-diol, used as starting material for the process, can be prepared by a method which can be illustrated as follows:

Pathway I:

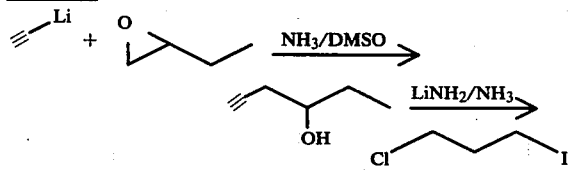

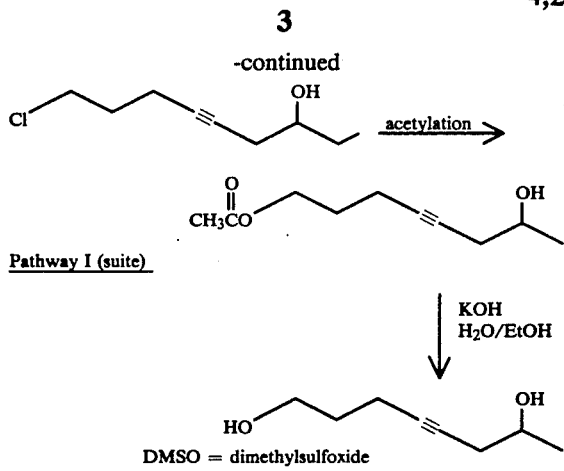

Pathway I (suite)

DMSO = dimethylsulfoxide

The following examples will describe in a more detailed way the above indicated preparative process.

EXAMPLE 1

2-Ethyl-1,6-dioxaspiro[4.4]nonane 0.540 g of mercury oxide in 100 ml of distilled water and 3.6 ml of concentrated $H_2SO_4$ were heated at 60° and at this temperature non-4-yn-1,7-diol (3.0 g) was added to the reaction mixture, which was then left 30 min under stirring. After cooling to room temperature, the mixture was extracted twice with diethyl ether washed with an aqueous solution of $NaHCO_3$ and brine until neutrality, and finally dried over $Na_2SO_4$. The volatiles were taken off by evaporation in vacuo and the obtained residue was distilled in a bulb apparatus. 2.3 g (yield 35.2%) of the desired 2-ethyl-1,6-dioxaspiro[4.4-]nonane having b.p. 80°-90°/1 Torr were thus obtained. The product had a purity of ca. 97%.

IR(neat): 3000, 2970, 2910, 1460, 1440, 1380, 1340, 1240, 1180, 1150, 1110, 1080, 1040, 1020, 960, 930, 920, 860 and 830 cm$^{-1}$;

NMR: 0.90 (3H, t, J=7 cps); 1.2-2.5 (10H); 3.9 (3H, m) δ ppm;

MS: M$^+$=156(1); m/e: 127 (100), 115 (5), 98 (30), 87 (45), 85 (40), 64 (16), 55 (29), 43 (35), 29 (28).

Non-4-yn-1,7-diol, used as starting material in the above given process, can be prepared as follows:

a. Hex-5-yn-3-ol 3.5 g (0.5 atg) of granulated lithium was added portionwise to 300 ml of liquid ammonia containing 1 crystal of $Fe(NO_3)_3$, whereupon the mixture was kept at reflux (−33°) until complete discoluration. 0.250 g of triphenylmethane were then added to the reaction mixture which thus required a pink colour and acetylene was passed through until novel discolouration has occured. After addition of 125 ml of anhydrous dimethylsulfoxide and slow evaporation of ammonia, the mixture was heated to ca. 15° and 36 g (0.5 M) of 1,2-butyleneoxide were added thereto, whilst the temperature was kept at 15°-20°. After having been stirred for 1¼ h, the reaction mixture was poured onto ice/water, saturated with $NH_4Cl$ and extracted 15 times with fractions of 50 ml each of diethyl ether. The ethereal extracts were dried over $Na_2SO_4$, concentrated and distilled to give 26 g (yield 54%) of hex-5-yn-3-ol.

IR(neat): 3400, 3330, 2980, 2950, 2900, 2125, 1460, 1420, 1240, 1110, 1100, 1060, 1020 and 980 cm$^{-1}$;

NMR(CDCl$_3$): 0.96 (3H, t, J=6 Hz); 1.3-1.9 (2H, m); 2.04 (1H, t, J=2 Hz); 2.35 (2H, J=6 Hz); 3.66 (1H, q, J=6 Hz) δ ppm;

MS: M$^+$=98 (0); m/e: 69 (6), 59 (100), 41 (42), 31 (60).

b. 9-Chloro-non-5-yn-3-ol 24.5 g (0.25 M) of hex-5-yn-3-ol in 30 ml of anhydrous tetrahydrofuran was added to 0.55 M of lithium amide prepared by dissolving 3.85 g of granulated lithium in 400 ml of liquid ammonia. The mixture was left at reflux during 3 h, whereupon a solution of 51.1 g of 1-chloro-3-iodopropane (0.25 M) in 50 ml of anhydrous tetrahydrofuran was added thereto. The mixture thus obtained was kept at reflux at −33° for 1½ h, then 100 ml of tetrahydrofuran, followed by portions of $NH_4Cl$ (20 g), were added thereto, and the whole was left on a water bath whilst ammonia was gradually taken off.

At about 0°, 100 ml of water were added dropwise to the reaction mixture which was then extracted with 3 fractions of diethyl ether. The combined organic extracts were washed, dried, evaporated and finally distilled through a Vigreux column.

8.0 g (yield 18.4%) of the title compound having a purity of about 95% at b.p. 125°-129°/11 Torr were collected. MS: M$^+$=174 (0); m/e: 116 (19), 88 (53), 81 (42), 67 (11), 59 (100), 41 (37), 31 (55).

c. 3-Hydroxy-non-5-yn-9-yl acetate

A mixture of 7.9 g (0.045 M) of the chloroalcohol, obtained in accordance with paragraph b. above, in 100 ml of dimethylformamide and 7.43 g of anhydrous sodium acetate (0.090 M) was heated at reflux for 2 hours. After cooling, the mixture was poured onto ice and extracted with 3 fractions of hexane whereupon the combined organic extracts were subjected to the usual treatments of washing, drying over $Na_2SO_4$, evaporation and bulb distillation.

5.2 g (yield 58%) of the title compound having a purity of 93% were thus obtained at b.p. 160°-180°/10 Torr.

NMR(CDCl$_3$): 0.96 (3H, t, J=6 Hz):, 1.3-2.0 (4H, m); 2.05 (3H, s); 2.2-2.5 (4H, m); 3.67 (1H, m); 4.20 (2H, t, J=6 Hz) δ ppm;

MS: M$^+$=198 (0); m/e: 140 (2), 125 (2), 109 (3), 98 (17), 89 (75), 79 (100), 59 (27), 43 (90), 31 (21).

d. Non-4-yn-1,7-diol

A mixture of 5.0 g (0.025 M) of 3-hydroxy-non-5-yn-9-yl acetate, 2.8 g (0.050 M) of KOH pellets in 10 ml of water and 50 ml ethanol was left stirring for 1 ¼ h at room temperature. The mixture was then acidified with 10% $H_2SO_4$, extracted with 3 fractions of diethyl ether and the combined organic extracts were subjected to the usual treatments.

Distillation through a bulb apparatus yielded 3.6 g (yield 91.4%) of the title compound having b.p. 110°-120°/0.4 Torr.

A further purification was achieved by column chromatography on $SiO_2$ (eluant: hexane/ether/ethanol, 6:3:1). 3.0 g of non-4-yn-1,7-diol was thus obtained; b.p. 110°/0.4 Torr.

NMR(CDCl$_3$): 0.93 (3H, t, J=6 Hz); 1.2-2.0 (4H, m); 2.29 (4H, m); 3.71 (3H, m) δ ppm;

MS: M$^+$=156 (1); m/e: 138 (56), 109 (4), 98 (55), 79 (87), 70 (100), 59 (75), 41 (63), 31 (71).

What we claim is:

1. A method of attracting insects of the order *Pityogenes chalcographus*, which comprises permeating the atmosphere in an area infested with said insects with an effective attractant amount of a compound of formula

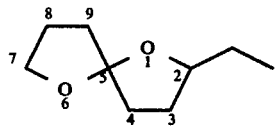

(I)

2. A method according to claim 1 which uses a composition comprising a suitable carrier substance and a compound of formula

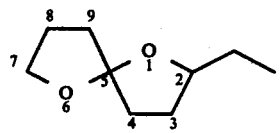

(I)

3. A method according to claim 1 in which the insects are the bark beetle species.

* * * * *